United States Patent [19]
Roos

[11] Patent Number: 5,269,780
[45] Date of Patent: Dec. 14, 1993

[54] ELECTRO-SURGICAL DEVICES

[75] Inventor: Eberhard Roos, Tuttlingen, Fed. Rep. of Germany

[73] Assignee: Delma elektro- und medizinische Apparatebau Gesellschaft mbH, Tuttlingen, Fed. Rep. of Germany

[21] Appl. No.: 767,161

[22] Filed: Sep. 27, 1991

[30] Foreign Application Priority Data

Oct. 12, 1990 [DE] Fed. Rep. of Germany ....... 4032471

[51] Int. Cl.⁵ .............................................. A61B 17/39
[52] U.S. Cl. ........................................ 606/42; 606/48; 606/50; 606/51
[58] Field of Search ........................ 606/42, 45, 46, 48, 606/49, 50, 51

[56] References Cited

U.S. PATENT DOCUMENTS

| | | | |
|---|---|---|---|
| 2,032,860 | 3/1936 | Wappler et al. | 606/46 |
| 2,056,377 | 10/1936 | Wappler | 606/48 |
| 4,016,881 | 4/1977 | Rioux et al. | 606/51 |
| 4,418,692 | 12/1983 | Guay | 606/51 |
| 4,671,274 | 6/1987 | Sorochenko | 606/51 |

FOREIGN PATENT DOCUMENTS 2415263 10/1975 Fed. Rep. of Germany ........ 606/51

*Primary Examiner*—Lee S. Cohen
*Attorney, Agent, or Firm*—Townsend and Townsend Khourie and Crew

[57] ABSTRACT

A electrosurgical device for selectively carrying out bipolar coagulation or tissue has a preferably elongate instrument housing (10) with a guide tube (14) for three mutually insulated contact rods (11, 12, 13) which are arranged therein. Two of the contact rods (12, 13) serve at their free ends as coagulation electrodes (22, 23) and the center one (11) serves as a cutting electrode (21) which can be moved towards or through the two coagulation electrodes. In this arrangement a switching device (16) is provided with the aid of which an Rf current suitable for bipolar coagulation can be applied to the coagulation electrodes (22, 23) in a first switch position. In a second switch position, the coagulation electrodes (22, 23) are connected in parallel while a potential suitable for tissue cutting is applied to the cutting electrode (21).

17 Claims, 3 Drawing Sheets

ELECTRO-SURGICAL DEVICES

BACKGROUND of the INVENTION

The invention relates to an electrosurgical device for selectively carrying out bipolar coagulation or tissue cutting.

In gynecology operations in the lower abdomen have been carried out for a long time with the aid of endoscopes which are inserted through the abdominal wall without opening the abdomen. In more recent time methods have been developed also in general surgery in which the surgical operation is effected with the aid of endoscopes.

Electrosurgical techniques with radio frequency current are in particular used in such operations, in particular for the coagulation of fallopian tubes, for surgical detachment (detachment of intergrowth between organs of the lower abdomen), for stopping bleeding during laparoscopic appendectomy and laparoscopic cholecystectomy or cholecystotomy.

Having regard to the unclear conductive conditions in the lower abdomen the bipolar method is thereby preferred, at least for carrying out coagulations, for which suitable electrosurgical devices or instruments exist. If however tissue cutting is to be carried out monopolar instruments in the form of needle or hook electrodes must generally be used. For this purpose it is necessary that the bipolar coagulation forceps introduced through a laparoscope are exchanged for corresponding monopolar cutting electrodes for which a significant time is required, which is undesirably long for surgical operations.

SUMMARY OF THE INVENTION

This invention relates to the electrosurgical device which can be selectively used for coagulation and for tissue cutting without requiring a lengthy electrode change.

This problem is solved by an electrosurgical device for selectively effecting polar coagulation or the cutting of tissue which a preferably comprises an elongate instrument housing on which a guide tube is arranged for three contact rods insulatedly arranged therein. Two of the contact rods serve at their free ends as coagulation electrodes and the third, in particular the central rod, serves as the cutting electrode which is movable by means of an actuation device towards or through the two coagulation electrodes. A switching means is provided to apply an Rf current suitable for bipolar coagulation to the coagulation electrodes in a first switching position, while connecting the coagulation electrodes in parallel in a second switching position, with a suitable potential for tissue cutting being applied to the cutting electrode.

Through the electrodes which are provided in accordance with the invention, of which two are formed as coagulation electrodes or neutral electrodes for tissue cutting and the third is formed as a cutting electrode for tissue cutting, and through the switching means for changing over from a coagulation operation to a cutting operation, it is ensured, in a surprisingly simple manner, that the electrosurgical device can be used both for bipolar coagulation and also for bipolar cutting without an interchange of the electrodes being necessary.

This arrangement, i.e. the present invention, has the special advantage that the surgeon, during an operation in which tissue cutting is necessary, can first coagulate the tissue to be cut in the region of the cut before cutting it through, so that the blood vessels in the cut zone are closed before the electro-cut is executed, so that practically no bleeding occurs.

The basic concept of the present invention is thus to be seen in that a third electrode is so arranged opposite to two electrodes lying alongside one another that a tissue to be coagulated or to be cut can be clamped in forceps-like manner between the electrodes, and in that, through an appropriate connection of the electrodes, which can be changed over by means of a switching device, it is possible to select between a coagulation operation and a cutting operation.

Through the arrangement of the Rf transformer in the handle or in the instrument housing it is possible for the Rf voltages required for bipolar coagulation and also for bipolar cutting to be supplied to the electrosurgical device from the outside via only two feed lines.

A further advantageous embodiment of the invention is characterized in that a winding ratio of approximately 1:1 exists between the primary winding of the Rf transformer and between the one end and the central tap of the secondary winding, and in that a winding ratio of at least 2:1 exists between the primary winding and the total secondary winding.

In order to make the change between coagulation operation and cutting operation as simple as possible even during a surgical operation there is preferably provided, in accordance with the invention, a cutting device which is characterized in that the switching device comprises a switch with a switch slider carrying contact springs which cooperates with a circuit board the contacts of which are connected to the electrodes and/or to the terminals in order, in the first switching position, to connect in each case one of the coagulation electrodes with the start and with the central tap of the secondary winding respectively, and, in the second switching position, to connect the two coagulation electrodes with the start and the cutting electrode with the end of the secondary winding.

It is in particular of advantage that the forceps-like movement between the cutting electrode and the coagulation electrodes takes place by means of the guide tube surrounding the corresponding contact rods, with the axial movement of the guide tube being translated into a radial forceps-like movement of the cutting electrode through the special layout of the cutting electrode.

In order to avoid short circuits on clamping tissue between the electrodes an insulated bent out portion of the cutting electrode is used in a particularly advantageous manner. It can be inserted between the coagulation electrodes, and serves in this way as a spacer.

The present invention further provides advantageous dimensions for the electrodes which ensure problem free and reliable operation. In this regard one aspect of the present invention provides that the ratio of the diameter of the contact rods forming the coagulation electrodes to the diameter of the contact rod forming the cutting electrode is at least 2:1. Preferably, this ratio is greater than 3:1 and, in particular, greater than 5:1. Another aspect of the invention provides that the ratio of the surfaces of the contact rods forming the coagulation electrodes to the surface of the contact rod forming the cutting electrode is at least 4:1.

DESCRIPTION OF THE PREFERRED EMBODIMENTS

Figure 1:
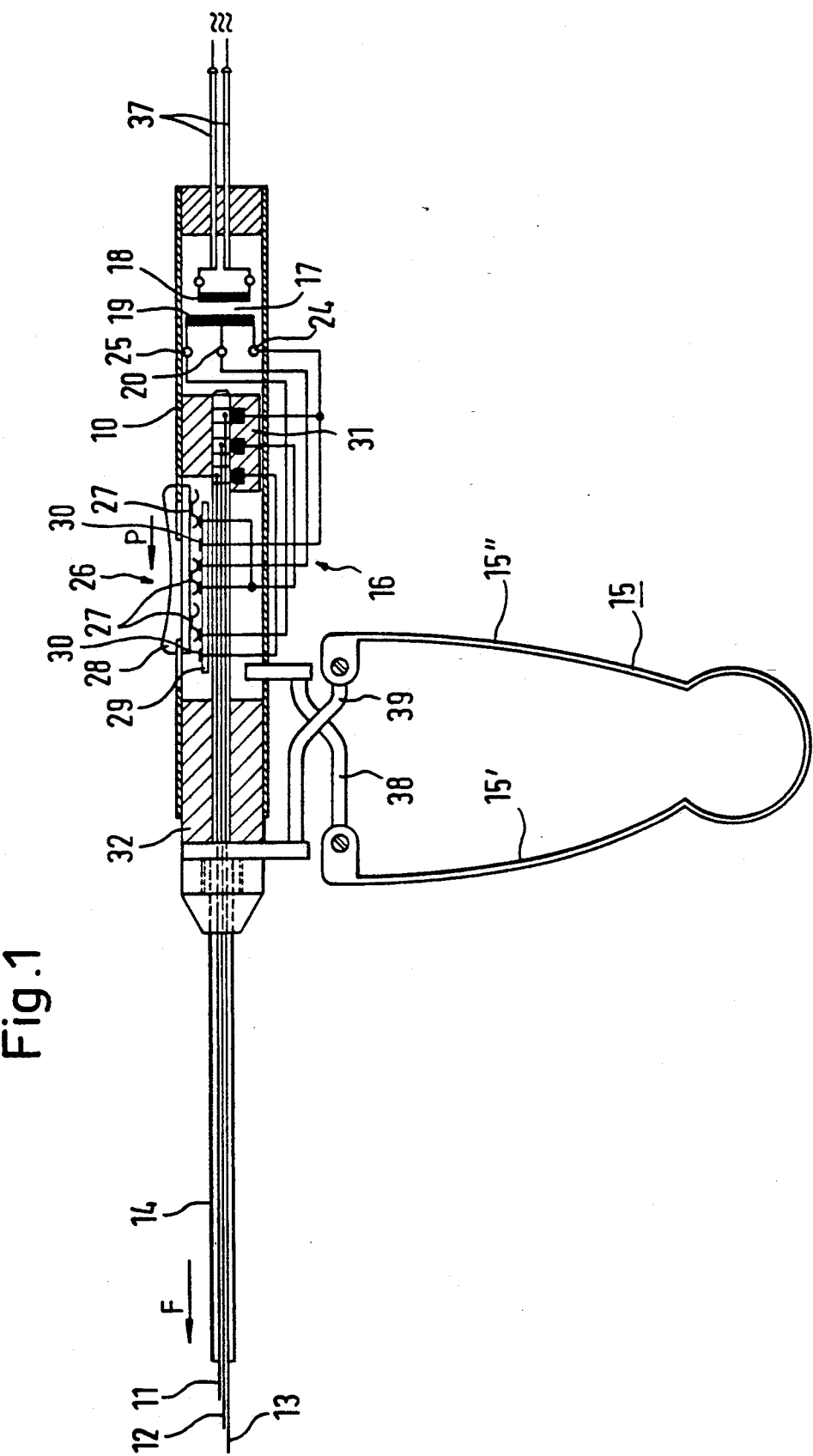
FIG. 1 is a schematic partly sectioned view of an electrosurgical device in accordance with the invention.
Figure 2:
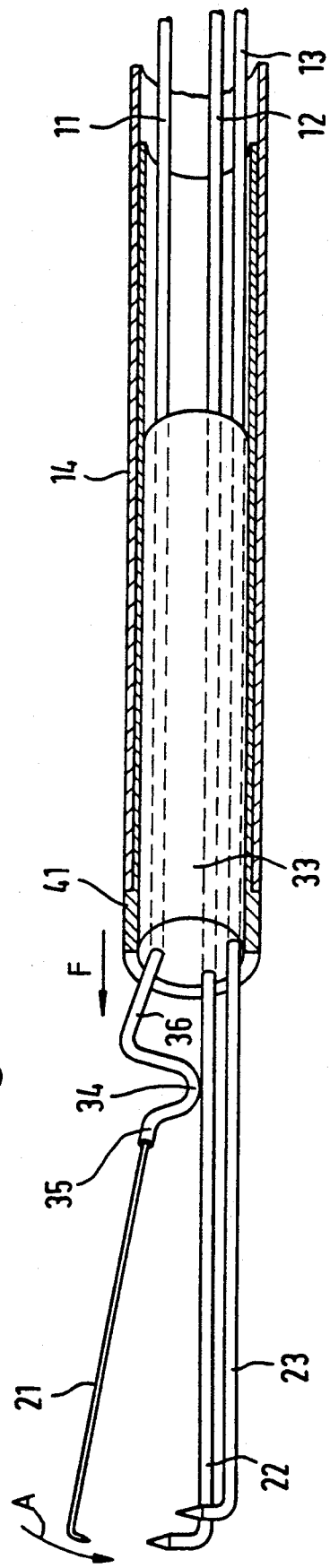
FIG. 2 is an enlarged partly sectioned perspective view of the front section of the electrosurgical device of FIG. 1.

FIG. 1 shows schematically an electrosurgical device in accordance with the invention with a tubular instrument housing 10 in which is arranged a switching device 16 and a slide member 32. A guide tube 14 is screwed onto the slide member 32 which is axially displaceably arranged in the instrument housing 10. Contact rods 11, 12, 13 extend through the guide tube 14 and the slide member 32 and—as shown in FIG. 2—carry at their front ends an upper electrode 21 and lower coagulation electrodes 22, 23 which are bent upwardly in hook-like manner. At their rear ends the contact rods 11, 12, 13 are so arranged in a contact clamping block 31 fixedly connected to the instrument housing 10 that they are firmly held in the instrument housing and so that they are electrically connected with the contacts of a circuit board 29.

The circuit board 29 is a part of the switching device 16 which includes a transformer 17, the primary winding 18 of which is connected via a line 37 with a non-illustrated electrosurgical radio frequency apparatus. The secondary winding 19 of the transformer 17 has a central tap 20 and is connected by the central tap and also the start 24 and end 25 to the contacts of the circuit board or printed circuit 29.

The circuit board 29 forms, together with a switching slide 28 carrying contact springs 27, a switch 26 which serves for changing over between coagulation operation and cutting operation.

If the switching slide 28 of the switch 26 adopts the position illustrated in FIG. 1 then the start 24 of the secondary winding 19 of the Rf transformer 17 is connected to the contact rod 13 while its central tap 20 is connected to the contact rod 12. In this switch position, which is intended for bipolar coagulation, the contact rod 11 is electrically separated from the end 25 of the second rewinding 19.

If the switching slide 28 is pushed forwardly in the direction of the arrow P, into its switching position associated with a cutting operation, then the contact rod 11 carrying the cutting electrode 21 is connected to the end 25 of the secondary winding of the HF transformer 17. Moreover the contact rod 12 is connected in just the same way as the contact rod 13 with the start 24 of the secondary winding 19.

As shown in FIG. 2 a guide sleeve 41 is inserted into the front free end of the guide tube 14 and an insulating member 33 is arranged with an axially sliding seat in the guide sleeve 41. The contact rods 11, 12, 13 extend through the insulating member 33 and are axially fixedly connected therewith, so that the insulating member 33 ensures the required spacing between the contact rods and the guide tube 14.

The contact rod 11 carries the cutting electrode 21 at its end which projects out of the insulating member 33 and out of the guide tube 14 and initially has an upwardly bent section 36 which merges into a downwardly directed bent portion 34 from which the cutting electrode 11 extends obliquely upwardly in relation to the plane determined by the contact rods 12, 13 or by the coagulation electrodes 22, 23.

An insulated hose 35 is drawn over the bent portion 34 and the upwardly bent section 36 of the contact rod 11. As a result the bent portion 34 acts as a spacer between the coagulation electrodes 22, 23 when the cutting electrode 21 is moved in the direction of the arrow A, downwardly, in forceps-like manner towards the coagulation electrodes 22, 23 due to the guide tube 14 being pushed forwardly in the direction of the arrow F.

For the displacement of the guide tube 14 relative to the electrodes 21, 22, 23 there is provided an actuating device which is formed as a spring handle 15. The first limb 15' of the spring handle 15 is connected via a connecting rod 38 with the instrument housing 10, while the second limb 15" is arranged via a connecting bar 39 on the slide member 32 which carries the guide tube 14. The limbs 15', 15" and the connecting bars 38, 39 of the spring handle 15 are so arranged that on pressing the spring handle 15 together the front limb 15' is held together with the instrument housing 10 and thus with the electrodes 21, 22, 23, whereas the displacement of the second rear limb 15 forwardly brings about a displacement of the guide tube 14 in the direction of the arrow F via the slide member 32.

The manner of operation of the described electrosurgical device will now be described with reference to FIG. 3, first of all for the process of a bipolar coagulation.

For carrying out a coagulation the switch slider 9 is located in the position illustrated in FIG. 1, so that the contact rod 12 and thus the one contact electrode 22 is connected to the central tap 20 and the other contact rod 13 or coagulation electrode 23 is connected to the start of the secondary winding of the Rf transformer 17. The winding ratio of the primary winding 18 relative to the section of the secondary winding between the start 24 and the central tap 20 thereby preferably amounts to approximately 1:1 so that the Rf voltage applied to the primary winding 18 is approximately applied to the coagulation electrodes, the diameter of which is however at least twice as large as the diameter of the cutting electrode, and is however preferably three times as large or larger.

Figure 3:
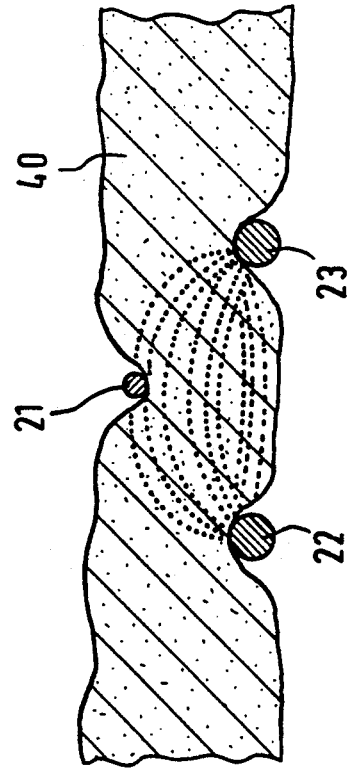
FIG. 3 is a schematic illustration of the current flow during bipolar coagulation.

As shown in FIG. 3 the tissue to be coagulated is now clamped between the coagulation electrodes 22, 23 and the cutting electrode which is electrically free. For this purpose the spring handle 15 is only partly compressed so that the guide tube 14 is only advanced forwardly so that the cutting electrode 21 just executes a forceps-like holding function.

If the Rf current is now switched on by means of the corresponding Rf apparatus then the current flux zone in the tissue 40 shown by the dotted current lines results between the contact electrodes 22, 23 in which the electrical heat loss necessary for coagulation arises when the current flux is sufficiently high.

Account must be taken of the fact that the power characteristic of the Rf circuit formed by the coagulation electrodes 22, 23, the tissue 40 clamped between them and the winding section Qf the secondary winding between the start 24 and the central tap 20 must be of a low resistance, so that the current flux tends to zero as the coagulation progresses with the associated drying out and increasing resistance of the tissue. Thus no sparks can occur at the transition from the coagulation electrodes 22, 23 to the tissue 40. If sparks were to form then an insulating crust of dried blood and/or secretion would form on the coagulation electrodes 22, 23 whereby the electrodes would become unusable for a second coagulation.

Figure 5:
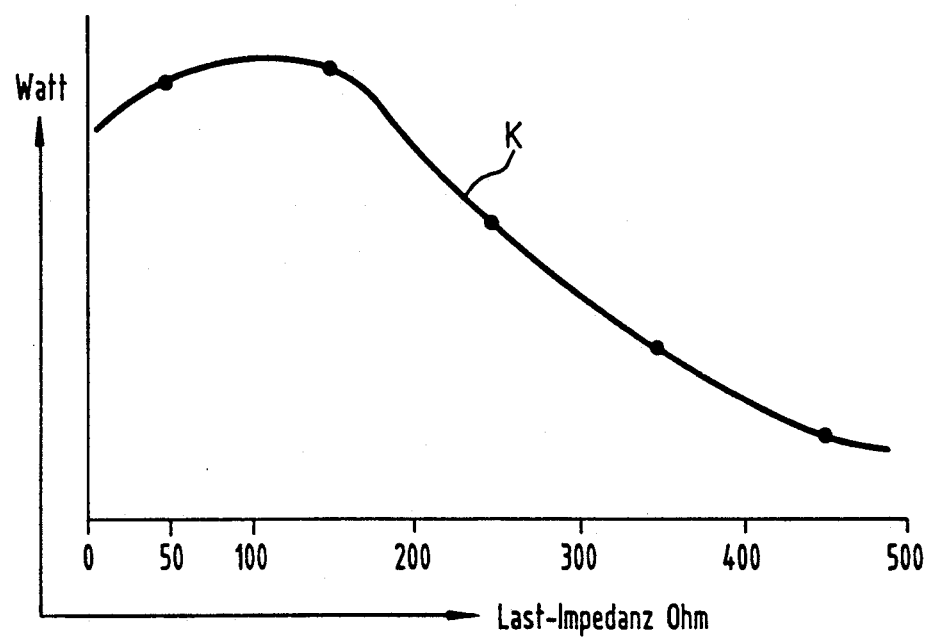

A corresponding low ohmic power characteristic for the coagulation is shown as curve K in FIG. 5 where the load impedance is shown in ohms on the abscissa whereas power is recorded on the ordinate.

If cutting is to be effected with the described electrosurgical device then the switch slider 28 is first pushed forwardly in the direction of the arrow P whereby the cutting electrode 21 is connected via the contact rod 11 with the end 25 of the secondary winding 19 of the Rf transformer 17. At the same time both coagulation electrodes 22, 23 are connected to the start 24 of the secondary winding 19.

Figure 4:
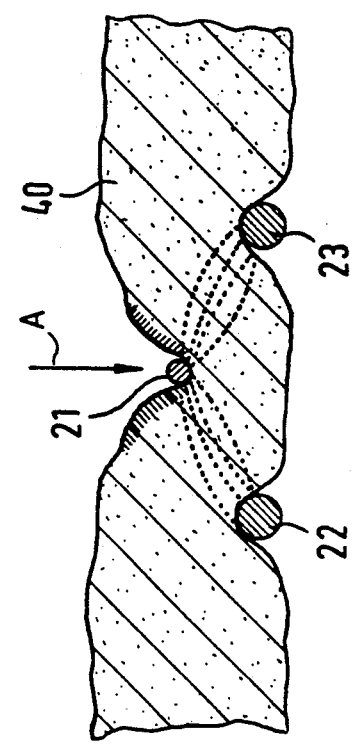
FIG. 4 is a schematic view of the current flow during bipolar cutting, FIG. 5 a schematic illustration of the power characteristic for bipolar coagulation.

For cutting the tissue to be cut will now be clamped between the coagulation electrodes 22, 23 and the cutting electrode 21 as shown in FIG. 4. As the diameter of the cutting electrode 21 is very much smaller relative to the coagulation electrodes 22, 23, which serve as neutral electrodes during bipolar cutting, the current density formed during current transfer from the cutting electrode 21 to the tissue 40 is many times higher than at the contact surfaces of the coagulation electrodes 22, 23, so that the heat lost in the tissue 40 in the region of the cutting electrode 21 is so high that the tissue cells are burst by vapor formation and the tissue parts or is cut there.

The tissue 40 clamped between the electrodes 21, 22, 23 is cut with the spring pressure exerted by means of the spring handle 15 via the guide tube 14 onto the cutting electrode 21. In this arrangement the contact rod 11 is set into up and down movements by opening and closing of the spring handle 15 so that the surgeon can cut through the tissue in similar manner to using a pair of scissors.

In this arrangement the switching device provided in accordance with the invention for changing over between coagulation and cutting is particularly advantageous since it is hereby possible to carry out a coagulation in accordance with FIG. 2 before the described cutting process in accordance with FIG. 3 so that the blood vessels lying in the cutting zone are closed and the electro-cut cannot cause any bleeding.

Figure 6:
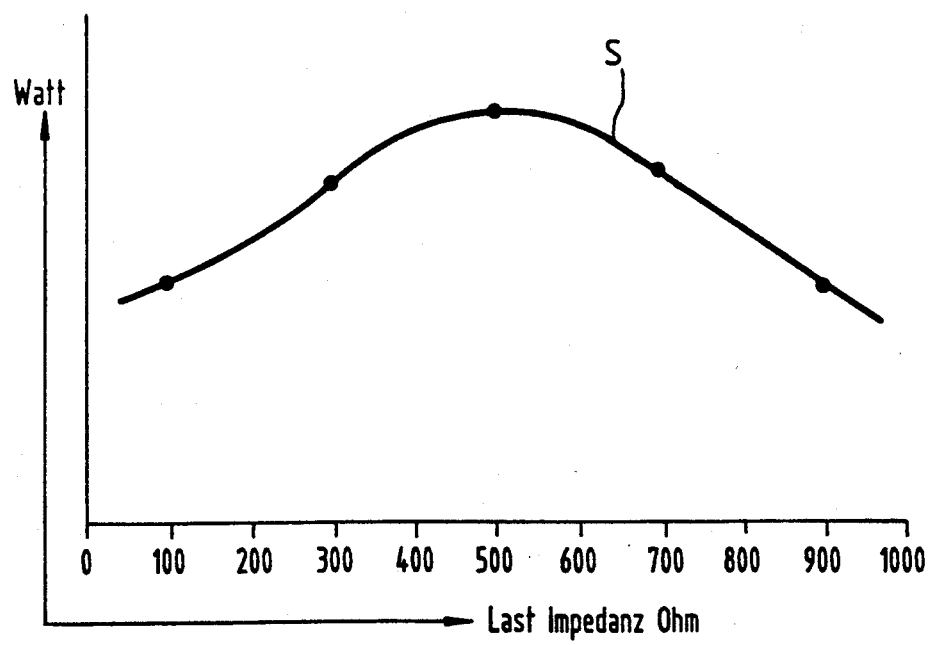
FIG. 6 is a schematic illustration of the characteristic for bipolar cutting.

For trouble-free tissue cutting it is necessary that the power characteristic of the Rf circuit comprising the cutting electrode 21, the coagulation electrodes 22, 23, the tissue 40 and the secondary winding 19 of the Rf transformer 17 is highly resistive, so that at the expected load impedances of about 300 ohms to 600 ohms the high frequency power necessary for cutting is available. For rapid cutting this power amounts to about 50 watts. Thus, with an assumed load impedance of 500 ohms a voltage of 160 volts results which is generated by the total secondary winding 19 of the transformer 17. This elevated voltage ensures a current flow through the tissue, even when the cutting electrode is encrusted or oxidized, which cannot be avoided during cutting. A power characteristic suitable for tissue cutting is shown as the curve S in FIG. 6. In this arrangement, in accordance with FIG. 5, the load impedance is recorded on the abscissa and the power on the ordinate.

During cutting neither spark formation nor a cutting effect can arise at the coagulation electrodes 22, 23 which serve as neutral electrodes for the bipolar cutting. This is because the substantially larger diameter of these electrodes 22, 23 and their connection in parallel means that the current density at the contact surfaces to the tissue remains well below the critical level.

Through the arrangement of the cutting electrode, which points obliquely upwardly in its rest position as shown in FIG. 2, there is the further advantage that the contact surface between the cutting electrode 21 and the tissue 40 is initially relatively small. Thus the current density in the region of the cutting electrode 21 is sufficiently high to initiate the cutting process despite the applied low Rf voltage.

At the start of the cutting process a relatively low Rf voltage is required since on placing the cutting electrode on the tissue a direct ohmic contact is first established. In this case a linear almost real load is present.

If the Rf current is switched on, and if the current flux is sufficiently large, cell fluid vaporizes in the tissue 21 contacting the cutting electrode 21 so that the tissue cells are burst by vapor pressure and the tissue separates. In this way the direct contact between the cutting electrode 21 and the tissue 40 is lost so that the impedance in the cutting current circuit becomes immediately larger, i.e. higher ohmic, and the voltage delivered by the generator of the Rf apparatus must increase.

In so doing the electrical field between the cutting electrode 21 and the tissue 40 also increases so that a glow discharge, or, with an appropriate energy density, an arc can form between the cutting electrode 21 and the tissue 40.

The cutting electrode can be easily guided without pressure through the tissue 40.

The high ohmic power characteristic of the Rf circuit shown in FIG. 5 is necessary so that a cutting process which takes place in this sequence can be carried out.

What is claimed is:

1. An electrosurgical device for selectively effecting bipolar coagulation or cutting of tissue, the device comprising an elongate instrument housing (10) including a guide tube (14); first, second and third contact rods (11, 12, 13) insulated from each other and arranged in the guide tube, free ends of the first and second contact rods (12, 13) serving as coagulation electrodes (22, 23) and a free end of the third rod (11) serving as a cutting electrode (21); an actuation device (15) including means for moving the cutting electrode relative to the coagulation electrodes (22, 23); and a switching device (16) including means for applying an Rf current suitable for bipolar coagulation to the coagulation electrodes (22, 23) in a first switching position, for connecting the coagulation electrodes (22, 23) in parallel in a second switching position, and for applying a potential for tissue cutting to the cutting electrode (21).

2. An electrosurgical device in accordance with claim 1 including an Rf transformer (17) operatively connected to the switching device (16), and arranged in the instrument housing (10), the transformer including a secondary winding (19) having a central tap (20).

3. An electrosurgical device in accordance with claim 2, wherein the Rf transformer has a winding ratio of approximately 1:1 between a primary winding (18) of the Rf transformer (17) and between one end terminal

(24) and the central tap (20) of the secondary winding (19), and wherein the Rf transformer has a winding ratio of at least 2:1 between the primary winding (18) and the secondary winding (19) of the Rf transformer.

4. An electrosurgical device in accordance with claim 3, wherein the switching device (16) comprises a switch (26) including a switch slider (28) carrying contact springs (27) and a circuit board (29) cooperating with the switch slider and having contacts (30) connected with the electrodes (21, 22, 23) and the Rf transformer so that, in the first switching position, one of the coagulation electrodes (22, 23) is connected with the end terminal (24) and another of the coagulation electrodes with the central tap (20) of the secondary winding (19), respectively, and, in the second switching position, the coagulation electrodes (22, 23) are connected with the end terminal (24) and the cutting electrode (21) with another end terminal (25) of the secondary winding (19).

5. An electrosurgical device in accordance with claim 1, including a contact clamping piece (31) fixedly attached to the instrument housing (10) in electrical connection with the switching device (16), the contact rods being secured to the clamping piece.

6. An electrosurgical device in accordance with claim 1, wherein the guide tube (14) is axially displaceable relative to the instrument housing (10) and the contact rods (11, 12, 13).

7. An electrosurgical device in accordance with claim 6, including a slide member (32) axially displaceable relative to the instrument housing, the guide tube being secured to the slide member, a forceps-like handle (15) for intentional displacement of the guide tube (14) relative to the instrument housing and having one limb (15') connected to the instrument housing (10) and another limb (15'') connected to the slide member (32).

8. An electrosurgical device in accordance with claim 7 wherein the forceps-like handle (15) is formed as a spring handle.

9. An electrosurgical device in accordance with claim 1, including an insulating piece (33), the contact rods (11, 12, 13) passing through the insulating piece (33) and at least axially fixedly connected to the latter, the insulating piece (33) being axially displaceably arranged in the guide tube.

10. An electrosurgical device in accordance with claim 1, wherein the third contact rod (11) forming the cutting electrode (21) has an insulated bent out portion (34) shaped so that a downward movement brought about by displacement of the guide tube (14) forms a spacer between the first and second contact rods (12, 13) forming the two coagulation electrodes (22, 23).

11. An electrosurgical device in accordance with claim 10, including an insulating hose (35) covering the bent out portion (34) of the third contact rod (11).

12. An electrosurgical device in accordance with claim 1, including an insulating piece (33) through which the third contact rod (11) forming the cutting electrode (21) extends, the third contact rod having an upwardly pointing bent section (36) guided out of the insulating piece (33) so that on advancing the guide tube (11) a forceps-like downward movement of the cutting electrode (21) formed by the third contact rod (11) is brought about relative to the coagulation electrodes (22, 23) formed by the first and second contact rods (12, 13).

13. An electrosurgical device in accordance with claim 1, wherein the first and second contact rods (12, 13) forming the coagulation electrodes (22, 23) have a larger diameter than the cutting electrode (21) formed by the third contact rod (11).

14. An electrosurgical device in accordance with claim 13, wherein a ratio of the diameter of the first and second contact rods (12, 13) forming the coagulation electrodes to the diameter of the third contact rod (11) forming the cutting electrode is at least 2:1.

15. An electrosurgical device in accordance with claim 14 wherein said ratio is greater than 3:1.

16. An electrosurgical device according to claim 14 wherein said ratio is greater than 5:1.

17. An electrosurgical device in accordance with claim 1, wherein a ratio of the surfaces of the first and second contact rods (12, 13) forming the coagulation electrodes (22, 23) to the surface of the third contact rod (11) forming the cutting electrode is at least 4:1.

* * * * *